United States Patent [19]
Wieszt

[11] Patent Number: 5,980,378
[45] Date of Patent: Nov. 9, 1999

[54] ARRANGEMENT AND PROCESS FOR THE VENTILATION OF A VEHICLE INTERIOR AS A FUNCTION OF HARMFUL GASES

[75] Inventor: Herbert Wieszt, Grafenau, Germany

[73] Assignee: DaimlerChrysler AG, Germany

[21] Appl. No.: 09/079,229

[22] Filed: May 15, 1998

[30] Foreign Application Priority Data

May 15, 1997 [DE] Germany .......................... 197 20 293

[51] Int. Cl.$^6$ ................................................. B60H 1/26
[52] U.S. Cl. ............................................. 454/75; 454/139
[58] Field of Search ...................................... 454/75, 139

[56] References Cited

U.S. PATENT DOCUMENTS

| | | | |
|---|---|---|---|
| 4,992,965 | 2/1991 | Holter et al. | 454/139 X |
| 5,259,813 | 11/1993 | Abthoff et al. | 454/75 |
| 5,320,577 | 6/1994 | Tooru et al. | 454/75 |
| 5,377,528 | 1/1995 | Dauvergne | 454/75 X |

FOREIGN PATENT DOCUMENTS

| | | |
|---|---|---|
| 29 41 305 | 10/1979 | Germany . |
| 42 17 394 A1 | 12/1993 | Germany . |
| 5-221231 | 8/1993 | Japan . |

*Primary Examiner*—Harold Joyce
*Attorney, Agent, or Firm*—Evenson, McKeown, Edwards & Lenahan, P.L.L.C.

[57] ABSTRACT

A method and apparatus for ventilation of a vehicle interior which can be switched between an incoming air operating mode and a circulating air operating mode as a function of harmful substances. The incoming-air concentrations of several harmful gases are measured and are separately evaluated. In each case either an incoming air operation request or a circulating air operation request is generated. A circulating air operation adjustment command is generated if the analysis for at least one of the harmful gases results in a circulating air operation request. The incoming air operation the vehicle-interior concentration of each harmful gas is estimated continuously as a function of the pertaining measured incoming-air concentration and of an incoming air rate, and a circulating air operation adjusting command is generated if the estimated interior concentration of at least one harmful gas rises at a rate which exceeds a definable threshold value.

4 Claims, 2 Drawing Sheets

ARRANGEMENT AND PROCESS FOR THE VENTILATION OF A VEHICLE INTERIOR AS A FUNCTION OF HARMFUL GASES

BACKGROUND AND SUMMARY OF THE INVENTION

The invention relates to a method and apparatus for ventilating a vehicle interior, which can be switched between an incoming-air operating mode and a circulating-air operating mode, in reference to detection of harmful gases.

For simplicity, the term "circulating-air operation" as used herein also includes an operating situation with a switched-off fresh-air operation without active circulation of the air of the vehicle interior. That is, the invention is also suitable for vehicles which do not have devices for active circulation of the air of the vehicle interior with the incoming air blocked (when the fresh-air supply is blocked).

U.S. Patent Document U.S. Pat. No. 5,320,577 discloses a method and apparatus of this generic type, in which a first gas sensor based on $WO_3$ is used to measure the concentration of diesel exhaust gas (specifically nitrogen oxides), and a second gas sensor based on $SnO_2$ is used to measure the concentration of flammable fuel vapors (specifically of hydrocarbons and carbon monoxide) contained therein. The two sensor output signals are analyzed in a special manner based on a calculation of the first and the second time derivatives. Circulating air operation is adjusted when the second derivative of the output signal of the CO and HC sensor is at least as large as a first threshold value, or when the second derivative of the output signal of the $NO_x$-sensor is smaller than or equal to a negative second threshold value and simultaneously the second derivative of the CO and HC sensor is at least as large as a third threshold value. In each case, circulating air operation is maintained for a time period which is determined as a function of the absolute value of the height and width of the pertaining maximum of the time derivative of the CO and HC sensor signal, or analogously of the value, the height or the width of the pertaining minimum of the time derivative of the $NO_x$, sensor signal.

German Patent Document DE 29 41 305 A1 discloses an arrangement for ventilating a vehicle interior which contains an outside (that is, an incoming-air) sensor, as well as a vehicle-interior sensor for measuring the harmful-substance concentrations of the outside air and of the inside air. The two measured harmful-substance concentration values are compared with respective threshold values, and the ventilation of the interior is control based thereon.

German Patent Document DE 42 17 394 A1 describes a process for ventilating a vehicle interior in which the harmful-substance concentration of the outside air is determined by a sensor, while the harmful-substance concentration of the inside air is computed by means of a model equation. The air quantity in the vehicle interior, the $CO_2$ entering from the outside, the $CO_2$ entering from the occupants and the $CO_2$ exiting to the outside are taken into account in a special manner. Alternatively, the $CO_2$ concentration in the interior is measured by means of a $CO_2$-sensor. As far as the occurrence of different harmful gases is discussed there, a weighting of the latter is suggested according to their effect on the human organism, and a single weighted harmful substance concentration value which represents the different harmful gases is then obtained.

An interruption of the fresh air supply (that is, a switch-over from incoming air operation to circulating air operation) in the sense of the present invention is triggered when the time variation of the sensor signal has reached or has fallen below a threshold value. The fresh air supply can then be re-opened as soon as the difference between the actual sensor signal value and the sensor signal value during the interruption of the fresh air supply, divided by the last-mentioned signal value, has reached or exceeded a second definable negative threshold value. The two threshold values vary as a function of the harmful-substance concentration of the inside air determined by way of the model equation, and are used to adjust the air.

One object of the invention is to provide a method and apparatus of the initially mentioned type for ventilating a vehicle interior, which permit, at relatively low expenditures, a switch-over between incoming air operation and circulating air operation, which can be individually adapted to various harmful gases, and can also respond to low concentrations of specific harmful gases.

This and other objects and advantages are achieved by the method and apparatus according to the invention, which provides several sensors, one for measuring the incoming-air concentrations of each one of various harmful gases. Operating mode control devices determine the interior concentration of each of these harmful gases individually, without requiring interior harmful gas sensors. The latter determination is made by continuous estimation, based on the harmful gas concentrations measured on the incoming air side, and on the incoming air flow rate (that is, the fresh air quantity per unit time which is guided into the vehicle interior). In this manner, the expenditures for the vehicle-interior-side harmful gas sensors can be eliminated.

The operating mode control devices evaluate the harmful gas concentration, measured on the incoming air side, separately for each of the harmful gases, and generate either an incoming air operation request or a circulating air operating request. The latter signals are evaluated in a logical OR-addition, and a circulating air operation adjustment command is generated if the evaluation of at least one of the harmful gases results in a circulating air operation request. The circulating air operation adjustment command, which is optionally linked to the existence of additional conditions, will then trigger an adjustment of the circulating air operation. Specifically, during an incoming air operation phase the operating mode control devices will generate the circulating air operation adjustment command if the estimated vehicle-interior concentration of at least one of the harmful gases rises at a rate which is above a definable threshold value. This switch-over criterion implicitly also takes into account the incoming-air concentration of the concerned harmful gas, because it enters into the estimation of the vehicle-interior harmful gas concentration.

By evaluating the harmful gas concentrations individually for each harmful gas, those specific harmful gases can also appropriately be taken into account which, compared with other harmful gases, occur in a lower concentration but have a comparably damaging influence. The logic combination of the evaluation results for the individual harmful gases ensures that a switch to circulating air operation is performed even though it is indicated by only one of the several harmful gases.

In one embodiment of the invention the operating mode control devices are designed so that, during circulating air operation, they continuously increase the vehicle-interior concentration of the respective harmful gas by a definable increment in order to estimate the deterioration of the air quality of the vehicle interior, in a simple and appropriate manner and without the requirement that it be detected by sensors. A switch-over command to incoming air operation is generated by the operating mode control devices when all estimated incremented harmful gas concentrations during a definable suitable waiting period are higher than the associated measured incoming-air harmful gas concentrations. The suitable waiting period prevents undesired brief switch-overs to incoming air operation followed by an immediate back to circulating air operation.

Other objects, advantages and novel features of the present invention will become apparent from the following detailed description of the invention when considered in conjunction with the accompanying drawings.

DETAILED DESCRIPTION OF THE DRAWINGS

Figure 1:
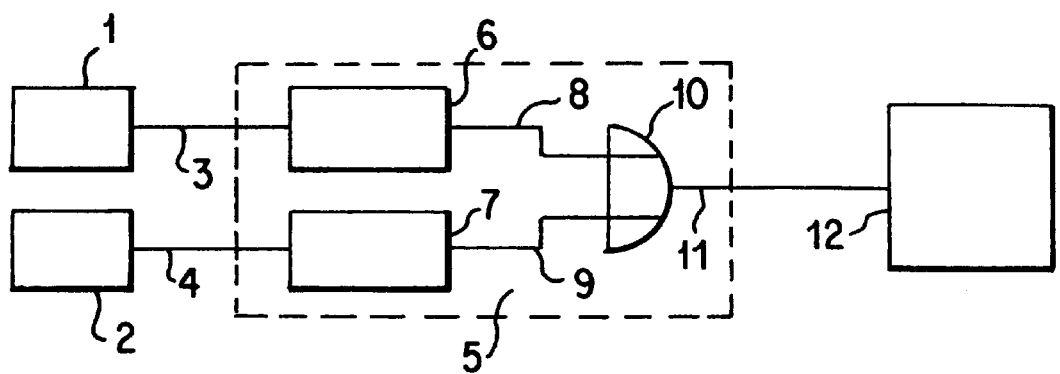
FIG. 1 is a schematic block diagram of an arrangement according to the invention for ventilating a vehicle interior.

The arrangement illustrated in FIG. 1 for ventilating a vehicle interior contains an incoming-air $NO_x$-sensor 1 and an incoming-air CO-sensor 2, which are conventionally positioned at a suitable point in the flow path of fresh air taken into the ventilating device. The two sensors 1, 2 thus sense separately the $NO_x$ and CO concentrations of the outside air blown as fresh air into the vehicle interior during incoming air operation. Each sensor emits an output signal 3, 4 containing pertinent harmful gas concentration information.

The two sensor output signals 3, 4 are fed to operating mode control devices in the from of a ventilation control unit 5, which comprises two analysis units 6, 7 (implemented in hardware or software) that evaluate individually each of the two sensor output signals 3, 4. Each of the analysis units 6, 7 generates and outputs an analysis signal 8, 9 which can take on one of two digital values. One signal level represents an incoming air operation request and the other signal level represents a circulating air operation request. The two analysis signals 8, 9 are fed in parallel to a (hardware or software) logic addition step 10, of the ventilation control unit 5 where they are combined in a logic addition to generate an operating mode selection signal 11. The operating mode selection signal 11 is fed from the ventilation control unit 5 to a vehicle interior ventilation adjusting device 12 which may contain, for example, a so-called circulating air flap. When the flap is open, fresh air can be taken in in the incoming air operation, and when it is closed it blocks off the fresh air supply (corresponding to the circulating air operation). If corresponding circulating devices exist and are activated, it simultaneously releases an active circulation of the air in the vehicle interior. In addition to being linked to the above-mentioned conditions for the switch-over between the incoming air operation and the circulating air operation, the adjustment of one or the other type of operation, according to the application, may be linked to additional conditions, in a manner known to a person skilled in the art.

Figure 2:
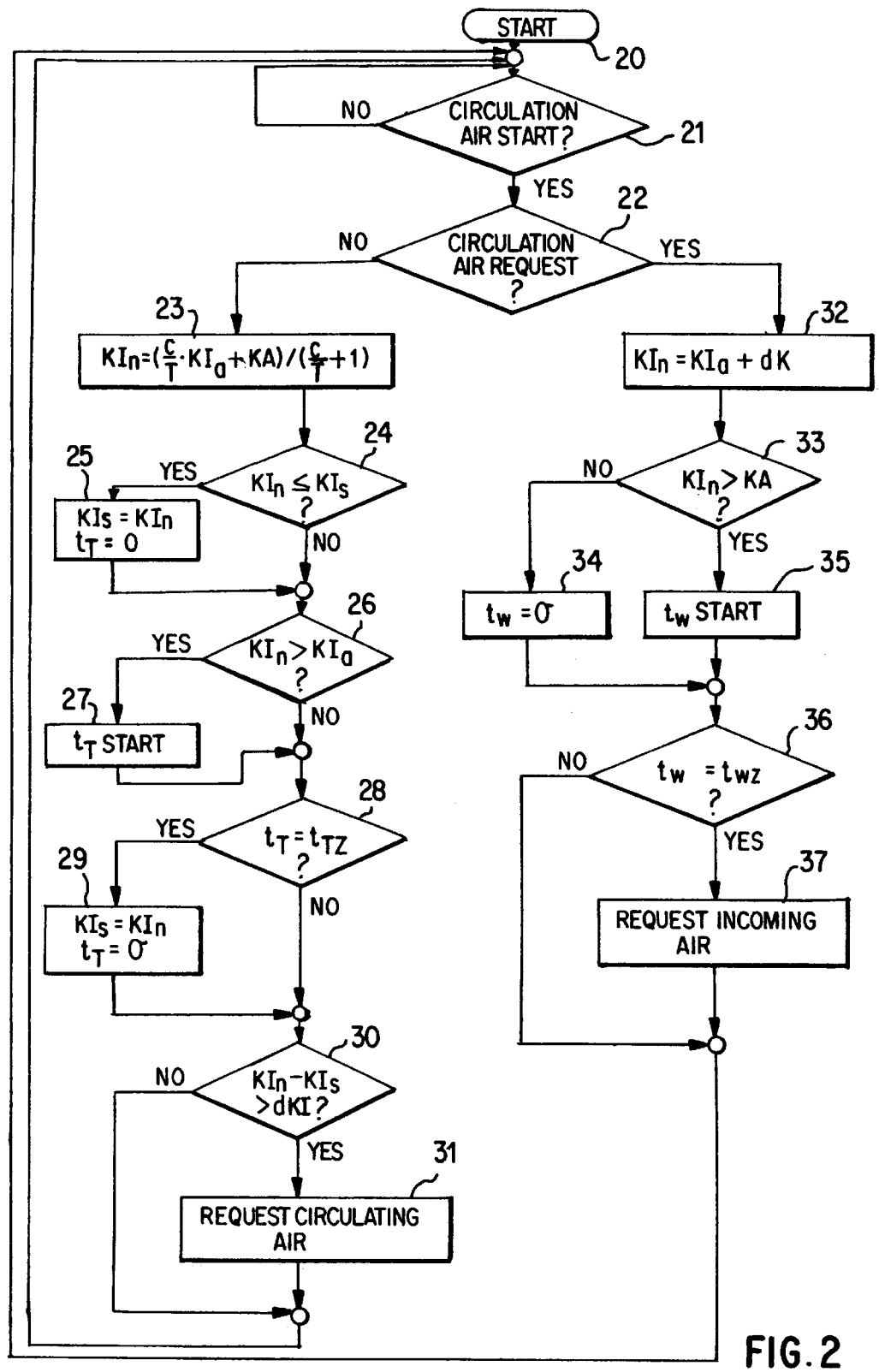
FIG. 2 is a flow chart which illustrates the method of operation of the arrangement of FIG. 1.

FIG. 2 illustrates the operating sequence (that is, the analysis operation) in the respective analysis unit 6 or 7. (The operating sequences of both analysis units 6, 7 are identical except that concentrations for different harmful gases are evaluated, and the numerical values of the different parameters and variables in the two cases will generally differ.) The process sequence illustrated in FIG. 2 is implemented in the respective analysis unit 6, 7 as software, and is repeated cyclically, for example, with a cycle time of 0.5s.

After the vehicle is started (step 20), it is first examined in step 21 whether defined circulating air operation starting conditions are present. These conditions may, for example, include the fact that a defined operation readiness waiting period has elapsed since starting of the vehicle, and when an air conditioner is being operated, the outside temperature is higher than a given threshold value, so that a harmful-gas-controlled circulating air operation at low temperatures and a resulting fogging-up of the vehicle windows is avoided. Expediently, a hysteresis may be provided for this outside-temperature-dependent enabling of circulating air operation, in order to avoid undesirably frequent switch-over between circulating air operation and incoming air operation when the outside temperature fluctuates about the threshold value. As long as the circulating air operation starting conditions do not exist, only the harmful gas concentrations of the outside air are measured by the sensors 1, 2 and the pertaining vehicle-interior harmful gas concentrations are computed by the analysis units 6, 7 in the manner described below, by means of an estimation. When an activated carbon filter is present, the circulating air operation starting criteria may also including the condition that the activated carbon filter operation is activated.

As soon as circulating air operation starting conditions exist, it is checked in a next query step 22 whether there is then currently a circulating air request (that is, whether the output signal 11 of the ventilation control unit 5 currently contains a circulating air operating adjusting command). If not, in a subsequent calculating step 23, the respective vehicle-interior harmful gas concentration KI, (that is, on the one hand, the vehicle-interior CO concentration $KI_{co}$ and, on the other hand, the vehicle-interior $NO_x$ concentration $KI_{nox}$)is calculated (by estimation) by the associated analysis unit 6, 7 used in this operating situation (activated incoming air operation).

The estimation provides a new determination of the respective vehicle-interior harmful gas concentration $KI_n$, in each new process cycle, based on the corresponding concentration value $KI_a$, of the measured momentary incoming-air concentration KA of the same harmful gas determined during the preceding process cycle; that is, on the one hand, the incoming-air $NO_x$ concentration $KA_{nox}$ measured by a sensor 1 and, on the other hand, the incoming-air CO concentration $KA_{co}$ measured by the other sensor 2, and a factor q representing the incoming air rate q, according to the equation $KI_n=(q \cdot KI_a+KA)/(q+1)$. The factor q representing the incoming air rate q can, for example, be indicated as a descending function of the output of an incoming air fan, with typical q-factor values in the range of between 10 and 20. During the first time process pass, the new vehicle-interior CO concentration or $NO_x$. concentration is set equal to the measured incoming-air-side CO concentration or $NO_x$ concentration.

The next steps in the incoming air operation mode determine whether the respective estimated vehicle-interior harmful gas concentration KI rises at a rate which exceeds a definable threshold value. For this purpose, a variable vehicle-interior concentration threshold value $KI_s$, is used which, during the first-time process pass and at the end of a respective circulating air operation phase, is set equal to the pertaining estimated vehicle-interior harmful gas concentration KI at the particular point in time. In an introductory query of this process section (step 24), it is determined whether the previous newly estimated vehicle-interior harmful gas concentration $KI_n$, is less than or equal to a variable threshold value $KI_s$. Only if this is so, the variable threshold value $KI_s$ is adjusted in a subsequent adjusting step 25 to the new vehicle-interior harmful gas concentration $KI_n$ and, in addition, a timer $t_T$ which counts a definable tolerance period $t_{TZ}$, is set to zero.

In each case this is followed by a query step 26 whether the newly estimated harmful gas concentration $KI_n$, is greater than the concentration $KI_a$ estimated in the preceding process cycle. If so, the time meter $t_T$ for counting the tolerance time period $t_{TZ}$ is started (step 27), and thereafter, it is queried in each case whether the counted value $t_T$ of this time meter has reached the tolerance time period $t_{TZ}$ (step 28). Only if this is so, in an adjusting step 29 which follows, the variable concentration threshold value $KI_s$ is adjusted to the newly estimated vehicle-interior harmful gas concentration $KI_n$, and the tolerance time period counted time value $t_T$ is set back to zero.

After this threshold value adjustment, it is then determined in step 30 whether the newly estimated vehicle-interior harmful gas concentration $KI_n$, has exceeded the relevant pertaining variable threshold value $KI_s$ by more than a given differential threshold value dKI. As a result of the above-mentioned adjustment of the variable threshold value $KI_s$, this can only be so if the estimated vehicle-interior harmful gas concentration KI has risen during the tolerance time period by more than the differential threshold value dKI (and thus at a rate which exceeds the threshold value). If this so, the respective analysis unit 6, 7 determines that circulating air operation is expedient, and generates an output signal 8, 9 at a level which corresponds to a request for circulating air operation (step 31). This completes a cycle of the incoming air operation process part, and the process returns to the point after the starting step 20 to implement the next process cycle.

If, in the circulating air query (step 22), an existing circulating air request is generated, in step 32, a new determination is made of the estimated vehicle-interior harmful gas concentration KI. In this case of circulating air operation this determination is made by increasing the vehicle-interior CO concentration or $NO_x$, concentration by a respective increment dK. By this estimation process, deterioration of the quality of the air in the vehicle interior due to $CO_2$ contamination from the vehicle occupants is taken into account.

According to the application, this incrementing can be carried out in every process cycle or only in each i-th cycle (i>1), in which case for successive incrementations, the increment itself and/or the cycle interval 1 can be selected to be variable. For example, during the initial vehicle operation phase, there may be a shorter interval than in the subsequent driving operation.

In a next step 33, it is inquired whether the newly estimated vehicle-interior harmful gas concentration $KI_n$, exceeds the associated measured momentary incoming-air harmful gas concentration KA. If not, the counted value $t_w$ of a time meter which is used for counting the waiting time period $t_{WZ}$, remains set at zero (step 34). However, if the newly estimated harmful gas concentration $KI_n$, has risen above the associated measured incoming-air harmful gas concentration KA, the waiting time period time meter $t_w$ is started (step 35).

Subsequently, it is inquired in step 36 whether the counted waiting time tw has reached the predetermined waiting time period $t_{WZ}$. If this is so, it can be concluded that the estimated vehicle-interior harmful gas concentration KI for a time period corresponding to the waiting time period $t_{WZ}$ has been higher than the pertaining measured incoming-air harmful gas concentration KA. Because the air quality of the vehicle interior is poorer than that outside the vehicle the respective analysis unit 6, 7 determines that a switch-over to an incoming air operation is expedient. It therefore generates an output signal 8, 9 on a signal level corresponding to an incoming air operation request (step 37). The waiting time period $t_{WZ}$ avoids undesirable short-term switch-over from circulating air operation to incoming air operation followed by an immediate switch back to circulating air operation when incoming air operation conditions are met for only a short time during a circulating air operation phase. The waiting time period $t_{WZ}$ can, for example, be on the order of between 10s and 20s. This terminates the circulating air portion of the process cycle, and a jump takes place to the point after the starting step 20, for implementing a new process cycle.

In the above-explained analysis of individual harmful gases in the respective analysis units 6, 7, the tolerance time period $t_{TZ}$, the differential threshold value dKI and (as required) also the other process parameters for the different harmful gases, can be set to different values adapted to the particular harmful gas. The logic addition step 10 which follows the two analysis units 6,7, prevents the ventilation control unit 5 from emitting an incoming air operation adjusting command at its output 11 before all estimated vehicle-interior harmful gas concentrations KI for the different harmful gases have been above the applicable measured harmful gas concentrations KA (and therefore all analysis units 6, 7 emit an incoming air operation signal level) for the waiting time period $t_{WZ}$.

The above description of an advantageous embodiment shows is that the invention provides a relatively simple method and apparatus which implements comparatively comfortable harmful-gas-dependent ventilation of the vehicle interior, taking several harmful gases individually into account in the decision whether to request incoming air operation or circulating air operation. It is understood that, according to the invention, the ventilation of the vehicle interior, and specifically the switch-over between the incoming air operation and the circulating air operation, can also be controlled in this manner as a function of the concentrations of harmful gases other than the two harmful gases CO and $NO_x$, indicated as examples. Of course, an arbitrary number of different harmful gases can also be taken into account, as required. For this purpose, the arrangement needs only be equipped with a corresponding number of incoming-air harmful gas sensors, and the ventilation control unit 5 must be designed correspondingly for parallel analysis of each of the different sensor output signals in the manner illustrated in FIG. 2. The logic addition step 10 must then correspondingly be designed with respective number of parallel inputs.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. Apparatus for controlling ventilation of a vehicle interior by a ventilation system which can be switched between an incoming-air operating mode and a circulating-air operating mode as a function of the detection of harmful gases, said apparatus comprising:

at least two incoming-air sensors for measuring the incoming-air concentrations of a corresponding number of different harmful gases; and operating mode control devices for controlling switching between said operating modes as a function of measured harmful gas concentrations, the operating mode control devices evaluating measured harmful gas concentrations separately for each harmful gas and in each case generating either an incoming air operation request or a circulating air operation request, said operating mode control devices generating a circulating air operation adjusting command if analysis results in a circulating air operation request for at least one of the harmful gases; wherein in the incoming air operation mode, the operating mode control devices continuously estimate the vehicle-interior concentration of each harmful gas as a function of incoming-air concentration thereof, measured by a respective incoming-air sensor, and of an incoming air rate (q), and generate a circulating air operation adjusting command for switch-over to the circulating air operation mode if estimated vehicle-interior concentration of at least one harmful gas rises at a rate which exceeds a definable threshold value.

2. Apparatus according to claim 1, wherein during circulating air operation the operating mode control devices continuously increase estimated vehicle-interior concentration of the respective harmful gases by a defined increment, and generate a command for a switch-over to the incoming air operation mode if estimated incremented concentration for each harmful gas has been higher than a measured incoming-air concentration for a defined waiting time period.

3. Process for ventilating a vehicle interior by means of a ventilation system which can be switched between an incoming air operating mode and circulating air operating mode as a function of harmful substances, said process comprising:

measuring incoming-air concentrations of at least two different harmful gases; and evaluating measured concentrations of each harmful gas separately;

for each harmful gas, generating either an incoming air operation request or a circulating air operation request; and generating a circulating air operation adjusting command if a circulating air operation request is generated for at least one of the harmful gases; wherein during an incoming air operation, the vehicle-interior concentrations of each harmful gas are continuously estimated as a function of the measured incoming-air-side concentration thereof, and of an incoming air rate (q), and a circulating air operation adjusting command is generated if the estimated vehicle-interior concentration of at least one harmful gas rises at a rate which exceeds a definable threshold value.

4. Process according to claim 3, wherein during circulating air operation estimated vehicle-interior concentration of the respective harmful gases is continuously increased by a definable increment, and a command for switch-over to incoming air operation is generated if an estimated incremented concentration for each harmful gas has been higher than a measured incoming-air-side concentration for a definable waiting time period.

* * * * *